United States Patent [19]
Wong et al.

[11] Patent Number: 6,123,827
[45] Date of Patent: Sep. 26, 2000

[54] METHOD FOR CALIBRATING SENSORS USED IN DIAGNOSTIC TESTING

[75] Inventors: David K. Wong, Del Mar; David Buse, La Jolla; Laurel Savage, Encinitas; Daiting Rong, San Diego, all of Calif.

[73] Assignee: Via Medical Corporation, San Diego, Calif.

[21] Appl. No.: 09/146,986

[22] Filed: Sep. 3, 1998

Related U.S. Application Data

[63] Continuation-in-part of application No. 08/783,944, Jan. 17, 1997, abandoned.

[51] Int. Cl.[7] .................................................... G01F 1/64
[52] U.S. Cl. ..................... 205/775; 204/415; 204/433; 205/783; 205/787.5; 436/9; 436/11
[58] Field of Search .................................... 204/415, 433; 205/787.5, 783, 775; 436/9, 11

[56] References Cited

U.S. PATENT DOCUMENTS

| | | |
|---|---|---|
| 4,573,968 | 3/1986 | Parker . |
| 4,734,184 | 3/1988 | Burleigh et al. . |
| 4,736,748 | 4/1988 | Nakamura et al. . |
| 4,786,394 | 11/1988 | Enzer et al. . |
| 4,871,439 | 10/1989 | Enzer et al. . |
| 5,132,000 | 7/1992 | Sone et al. . |
| 5,165,406 | 11/1992 | Wong . |
| 5,246,859 | 9/1993 | Nelson et al. . |
| 5,271,815 | 12/1993 | Wong . |
| 5,330,634 | 7/1994 | Wong et al. . |
| 5,431,174 | 7/1995 | Knute . |
| 5,505,828 | 4/1996 | Wong et al. . |

FOREIGN PATENT DOCUMENTS

WO 94/06019  3/1994  WIPO .

*Primary Examiner*—T. Tung
*Attorney, Agent, or Firm*—Sheppard, Mullin, Richter & Hampton LLP; James R. Brueggemann

[57] ABSTRACT

A method is disclosed for reliably calibrating a sensor used in diagnostic sensing of a predetermined parameter, e.g., $CO_2$ partial pressure, $O_2$ partial pressure, or pH, of a solution such as blood, the method compensating for expected variations over time in the value of the parameter in a calibration solution. The parameter of the calibration solution has a predetermined initial value, and the solution is initially located within a container that is configured to allow the value of that parameter to vary over time in a predetermined manner. Supplying the calibration solution to the sensor causes the sensor to produce a calibration solution signal, which is compared with a calculated value for the parameter based on its expected variation over time, to produce a calibration factor. Thereafter supplying the test fluid to the sensor causes the sensor produces a test fluid signal, and this test fluid signal then is adjusted in accordance with the calibration factor.

33 Claims, 3 Drawing Sheets

FIG. 4

METHOD FOR CALIBRATING SENSORS USED IN DIAGNOSTIC TESTING

This is a continuation-in-part of application Ser. No. 08/783,944, filed Jan. 17, 1997, now abandoned.

BACKGROUND OF THE INVENTION

This invention relates generally to the diagnostic testing of biological fluids and, more particularly, to the calibrating of sensors used in such testing.

Low-cost, disposable, electrochemical electrode assemblies have special utility as part of infusion fluid delivery systems commonly used in hospital patient care. Such systems infuse nutrients, medications, and the like directly into the patient at a controlled rate and in precise quantities, for maximum effectiveness. Such infusion fluid delivery systems are connected to a patient via an intravenous (IV) port, in which a hollow needle/catheter assembly is inserted into a blood vessel of the patient and thereafter an infusion fluid is introduced into the vessel at a controlled rate, typically using a peristaltic pump. Blood chemistry monitoring systems that are combined with infusion fluid delivery systems of this kind use the IV port to periodically withdraw a blood sample into an electrode assembly, perform measurements of blood ion concentrations and the like, and then discard the blood or reinfuse it into the patient. The system then resumes delivery of the infusion fluid.

The electrode assembly typically includes a reference electrode and a plurality of sensing electrodes, or sensors, that are each sensitive to a particular ion or species of interest. All of the electrodes are typically embedded in the base of the electrode assembly. For example, ion-selective electrodes generate electrical signals only in response to contact with the particular ion to which they are sensitive, and therefore provide selective measurement of the amount of that ion in the blood. This type of sensing electrode can be provided to measure, for example, blood calcium, hydrogen ion (i.e., pH), chloride, potassium, and sodium. In a differential measurement system, the reference electrode might be another ion-selective electrode (e.g., a chloride or sodium electrode) that is continuously exposed to a calibration or reference fluid. Alternatively, in a non-differential measurement system, a conventional reference electrode (which maintains a fixed potential when exposed either to reference fluid or to analyte) is required.

Presently employed electrochemical sensors for clinical diagnostic applications fall into three categories: ac impedance sensors, amperometric sensors, and potentiometric sensors.

An example of an ac impedance-type sensor is an hematocrit (Hct) sensor. Hematocrit is defined as the volume percent of red cells in the blood. Hematocrit can be determined by measuring the blood's ac impedance, using a pair of metal electrodes, typically at 1 kiloHertz (kHz).

An amperometric sensor produces an electrical current that varies with the concentration of a specific component of interest. For example, oxygen partial pressure (pO$_2$) and glucose (Glu) are commonly determined using amperometric sensors. An oxygen sensor assembly usually includes a working electrode formed from a noble metal, e.g., platinum or gold, and a suitable counter electrode formed of a different metal, e.g., silver/silver chloride. An oxygen-permeable, but liquid-impermeable, membrane is usually mounted over the sensor assembly, to separate the sample from the internal electrolyte and thereby avoid contamination. The sensor measures the limiting current of oxygen reduction at the working electrode according to the following equation:

$$O_2 + 2H_2O + 4e^- \rightarrow 4OH^-$$

This accomplished by applying a bias voltage of approximately 700 mV between the working (negative) electrode and the counter (positive) electrode. The resulting current is proportional to the pO$_2$ level in the sample.

The glucose sensor is very similar in construction to the oxygen sensor. One difference is that a hydrophilic membrane with immobilized glucose oxidase (i.e., GOD) is used instead of the hydrophobic oxygen membrane. In the presence of glucose oxidase, the following reaction occurs:

$$Glucose + O_2 \xrightarrow{GOD} Gluconic\ Acid + H_2O_2$$

In this case, glucose concentration can be determined by polarizing the working electrode either anodically or cathodically by approximately 700 mV, to measure the rate of hydrogen peroxide oxidation or oxygen reduction.

A potentiometric sensor produces an electrical voltage that varies with the species of interest. Ionic species, such as hydrogen ion (H$^+$), sodium (Na$^+$), potassium (K$^+$), ionized calcium (Ca$^{++}$) and chloride (Cl$^-$), are commonly measured by ion-selective electrodes, a typical class of potentiometric sensors.

The commonly used CO$_2$ sensor, sometimes known as the Severinghaus electrode, also is a potentiometric sensor (and is, in fact, essentially a modified pH sensor). Typically, it consists of a pH electrode and a reference electrode, with both covered by a hydrophobic, gas-permeable/liquid-impermeable membrane such as silicone. A thin layer of weakly buffered internal electrolyte. e.g., 0.001 M NaHCO$_3$, is located between the hydrophobic membrane and the pH sensing membrane. Carbon dioxide in the sample eventually reaches equilibrium with the internal electrolyte, and it produces a pH shift according to the following equation:

$$CO_2 + H_2O \rightarrow H^+ + HCO_3$$

The resulting pH shift is then measured by the pH electrode. Therefore, a direct relationship exists between a sample's CO$_2$ partial pressure (pCO$_2$) and its pH.

The accuracy of measurement obtained with any of the above-described sensors can be adversely affected by drift, particularly after exposure to biological fluids such as whole blood. Frequent calibration is therefore required. This is particularly true for gases such as pO$_2$ and pCO$_2$, because any change in the gas transport properties of the membrane can affect the sensor output.

To this end, a number of calibration fluids are usually needed. This is because at least two different calibrant concentration levels are usually required to characterize a sensor. For a multi-parameter system, it is sometimes impossible to use the same two solutions to calibrate all of the sensors, due to concerns such as chemical incompatibility and long term stability. Moreover, since it is technically difficult to maintain pCO$_2$ and pO$_2$ constant at desired calibration levels, most conventional blood chemistry analyzers carry two gas cylinders and several bottles of reagents just to fulfill the calibration requirements. This makes the analyzers bulky and cumbersome to use.

Attempts have been made to fill pre-tonometered liquid calibrants sealed into aluminum foil pouches under partial vacuum, as described in U.S. Pat. No. 4,734,184 to Burleigh. This approach has substantially reduced the blood chemistry analyzer's size and has improved the analyzer's portability. However, the contents of the pouch have a limited life after the pouch has been opened.

The current trend has been to move away from bench top analyzers toward the use of bedside analyzers. Moreover, instead of taking samples from the patients, sensors either are miniaturized and inserted into a blood vessel (in vivo) or are constructed as part of a flow cell connected to the patient end of an existing vascular access port (ex vivo), to provide continuous monitoring of blood chemistry.

The in vivo approach is conceptually more attractive, because it provides continuous results without intervention. However, it is considered more difficult to implement in practice, one major difficulty being blood clotting. Blood compatibility also has been a challenging issue. Even with a short term solution in hand, once sensors have been placed in the blood stream, repeated calibration becomes very difficult.

The ex vivo approach, originally described in U.S. Pat. No. 4,573,968 to Parker, employs a control unit to periodically draw a small amount of blood into contact with sensors that are incorporated into an in-line flow cell. After a measurement has been taken, the control unit resumes delivering physiological saline into the blood vessel. As a result, the blood drawn is effectively flushed back into the patient and the sensors are washed clean. U.S. Pat. No. 4,535,786 to Kater discloses a method to use an infusible IV saline solution to calibrate ionic species in the biological fluid. However, Kater fails to address the calibration of species such as $pO_2$ and $pCO_2$.

As mentioned above, blood chemistry sensors ordinarily require frequent calibration to maintain the accuracy of measurement. The calibration of pH and $pCO_2$ sensors remains a particular challenge. In aqueous solutions, these two parameters are inter-related by the following equation:

$$CO_2 + H_2O \rightarrow H^+ + HCO_3^-$$

At 37° C., the pH in a simple bicarbonate-containing physiological saline solution equal to:

Since the normal $pCO_2$ in arterial blood is approximately 40 mmHg, while the atmosphere contains 0.2–0.5 mmHg of $CO_2$, atmospheric $CO_2$ levels are not only too low, but they are also too variable to serve as a calibration point. An external $CO_2$ source is therefore required. Normally, the approach used in the art is to tonometer the solution with a known $CO_2$-containing gas and to then package the gas-equilibrated solution in a sealed container. This approach not only is costly, but also requires considerable effort to demonstrate that the solution can be safely infused.

U.S. Pat. No. 4,736,748 to Nakamura suggests that simultaneous calibration for $Na^+$, $K^+$, $Ca^{++}$, glucose, and hematocrit can be carried out using Lactated Ringer's solution with added glucose. However, such a solution could not be used for pH, $pCO_2$ and/or $pO_2$ calibration, because the solution has no well defined pH value or $pO_2$ value, and it contains essentially no $CO_2$. Indeed, since the amount of oxygen dissolved in Lactated Ringer's solution is not fixed (being a function of ambient temperature and barometric pressure—parameters which Nakamura does not contemplate monitoring), the patent fails to teach how to use the solution as an oxygen calibrant.

While the Burleigh patent identified above describes a solution that can be used for calibrating $CO_2$, the solution does not appear to be infusible. The patent fails to provide any guidance as to suitable calibration solutions for use with combined infusion fluid delivery/blood chemistry measurement system.

U.S. Pat. No. 5,132,000 to Sone et al. is similar to the Burleigh patent, in that it describes solutions that can be used for calibrating $CO_2$-containing solutions. However, the solutions do not appear to be infusible.

U.S. Pat. No. 5,505,828 to Wong et al. describes a calibration solution that is useful for calibrating an array of sensors capable of simultaneously measuring several blood chemistry parameters, including $pCO_2$ and $pO_2$, pH, sodium, potassium, ionized calcium, ionized magnesium, chloride, glucose, lactate, and hematocrit. Moreover, the solution is infusible, whereby it can facilitate calibration on a regular basis of all the sensors in the array, which is in constant fluid communication with the body.

The Wong et al. calibration solution works well for periods of time of up to about 8 hours. However, over longer periods of time, e.g., 12–24 hours, the solution's pH value will rise excessively, and its corresponding $pCO_2$ will drop excessively. This is due primarily to the diffusion of $CO_2$ from the infusion bag that initially carries the solution and from the IV set that carries the solution from the infusion bag to the sensor array. This variation in concentration can lead to significant calibration errors.

The Wong et al. calibration solution can function satisfactorily to calibrate $pO_2$, because concentration of $O_2$ in the solution is substantially the same as the concentration of $O_2$ in the atmosphere and because $O_2$ therefore will not diffuse from the infusion bag or the IV set. However, the amount of dissolved $O_2$ in the solution varies inversely with the solution's temperature. Consequently, if the solution delivered to the sensor array undergoes a sudden and significant temperature change, some of the dissolved $O_2$ will come out of solution and calibration errors can arise.

It should, therefore, be appreciated that there is a need for an improved method of calibrating sensors capable of measuring several blood chemistry parameters, including pH, $pCO_2$ and $O_2$, which can accommodate variations in the $pCO_2$ of a calibration solution due to diffusion of $CO_2$ from the solution's container, and which can accommodate significant variations in the temperature of the solution delivered to the sensors. The present invention fulfills this need.

SUMMARY OF THE INVENTION

The present invention resides in a method for calibrating a sensor of a kind that measures the value of a predetermined parameter (e.g., $CO_2$ partial pressure) of a test fluid such as blood, the method reliably compensating for expected variations over time in the value of the parameter in a calibration solution. The parameter of the calibration solution has a predetermined initial value, and the solution is initially located within a container that is configured to allow the value of that parameter to vary over time in a predetermined manner. The sensor to be calibrated is exposed to calibration solution supplied from the container, whereupon the sensor produces a calibration solution signal. The value of the parameter in the calibration solution supplied to the sensor is calculated based on its expected variation over time, and this calculated concentration is then compared with the calibration solution signal actually produced by the sensor, to produce a calibration factor. Further, the sensor then is exposed to the test fluid, whereupon the sensor produces a test fluid signal. Finally, the test fluid signal is adjusted in accordance with the calibration factor.

The method of the invention has particular utility as part of ay infusion fluid delivery and blood chemistry monitoring system, in which a puml ordinarily pumps the calibration solution from the container to a patient, via a sensor assembly that houses the sensor, whereupon the sensor produces the calibration solution signal. Periodically, the pump reverses its direction and draws blood from the patient into the sensor assembly, whereupon the sensor produces the test fluid signal.

The method is suitable for use in measuring the value of any parameter whose value in the calibration solution is subject to variation over time. It can be used, for example, with sensors that are sensitive to $CO_2$ partial pressure, pH, and $O_2$ pressure. $CO_2$ partial pressure and pH are subject to variation for their initial values, because the container has a porosity that allows $CO_2$ to escape from the solution until its partial pressure equilibrates with the $CO_2$ partial pressure of the surrounding atmosphere. $O_2$ partial pressure is subject to variation from its initial value according to temperature variations in the solution.

In some cases, the container for the calibration solution includes a flexible bag and an intravenous line. The flexible bag allows $CO_2$ to escape over time from the calibration solution it carries in a first predetermined manner, and the intravenous line allows $CO_2$ to escape over time from the calibration solution it carries in a second predetermined manner. In this case, when a $CO_2$ sensor is to be calibrated, the step of calculating includes calculating the concentration of $CO_2$ in the calibration solution supplied to the $CO_2$ sensor based on its expected escape over time from both the flexible bag and the intravenous line. Calculating also includes determining the time durations the calibration solution supplied to the $CO_2$ sensor has dwelled in both the flexible bag and the intravenous line. Calculating further includes measuring the temperature of the calibration solution in the container and determining the expected escape of $CO_2$ over time based on the measurec temperature.

The method can be used also to calibrate a pH sensor by compensating for variations in the pH of the calibration solution due to expected variations in the $CO_2$ partial pressure of the solution. In this case, the pH sensor is exposed to the calibration solution, whereupon the pH sensor produces a calibration solution pH signal, and the pH of the calibration solution supplied to the pH sensor is calculated based on the expected escape of $CO_2$ from the container over time. The calculated pH is then compared with the calibration solution pH signal actually produced by the pH sensor, to produce a pH calibration factor. The pH sensor also is exposed to the test fluid, whereupon the sensor produces a test fluid pH signal. Finally, the test fluid pH signal is adjusted in accordance with the pH calibration factor.

Other features and advantages of the present invention should become apparent from the following description of the preferred method, taken in conjunction with the accompanying drawings, which disclose by way of example the principles of the invention.

DESCRIPTION OF THE PREFERRED EMBODIMENT

Figure 1:
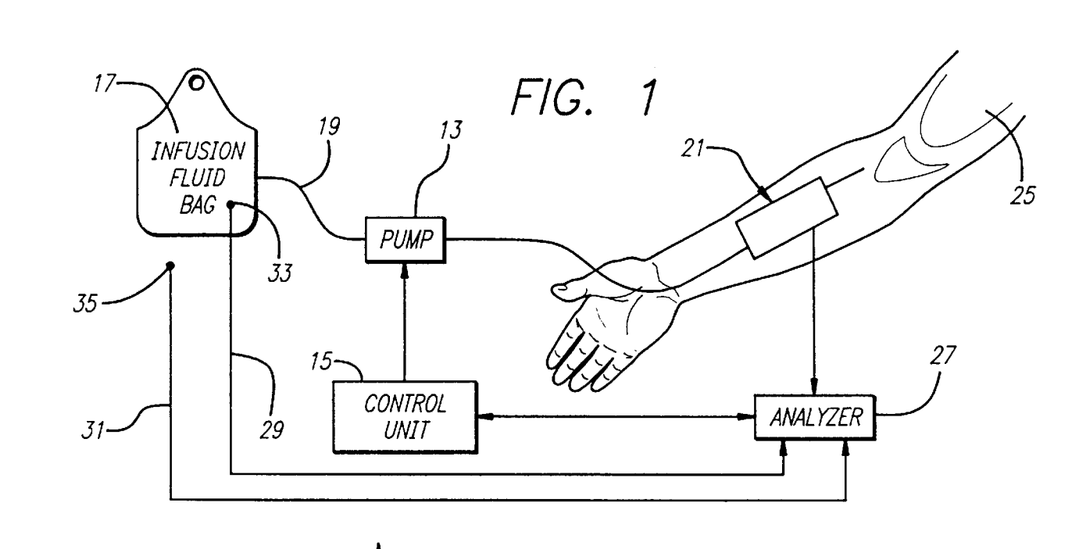
FIG. 1 is a simplified schematic diagram of a combination infusion fluid delivery and blood chemistry analysis apparatus useful in the practice of the present invention.

With reference now to the drawings, and particularly to FIG. 1, there is shown a combination infusion fluid delivery and blood chemistry analysis apparatus 11 useful in measuring various parameters of a patient's blood. The apparatus includes a peristaltic infusion pump 13 that is controllably conditioned by a control unit 15 so as to pump an infusion/calibration fluid, or calibrant, from an infusion fluid bag 17 through an intravenous (IV) set or line 19, a sensor assembly 21, and a needle/catheter assembly 23 to the patient 25. The control unit periodically conditions the pump to reverse its pumping direction and draw a predetermined amount of blood from the patient back through the needle/catheter assembly to the sensor assembly. After the sensor assembly has measured various parameters of the drawn blood, and these measurements have been stored and processed by an analyzer 27, the control unit conditions the pump to purge the blood from the sensor assembly back into the patient, and then to resume pumping the calibrant at its original controlled rate.

The sensor assembly 21 includes several individual sensors for measuring any of a number of various blood chemistry parameters. Such parameters can include, for example, hematocrit, glucose concentration, and various ionic concentrations such as sodium ion, potassium ion, calcium ion, and chloride. The individual sensors of the sensor assembly also can measure such blood chemistry parameters as pH, carbon dioxide partial pressure (pCO$_2$), and oxygen partial pressure (pO$_2$).

The various sensors of the sensor assembly 21 must be calibrated, for the signals they produce to have the requisite degree of accuracy. Calibration of the ion-sensitive sensors is achieved by formulating the calibrant initially carried in the bag 17 to include prescribed concentrations of various ions, including hydrogen, sodium, potassium, calcium and chloride. An analyzer monitors the voltage or current signals produced by these sensors when the calibrant is being pumped through the sensor assembly, so that the sensors' sensitivities can properly be characterized and calibrated.

Calibrating the $CO_2$ sensor of the sensor assembly 21 has in the past been a particularly difficult problem, typically requiring the use of bulky gas cylinders and bottles of reagents. An improved technique is disclosed in U.S. Pat. No. 5,330,634 to Wong et al., wherein a special infusible calibration solution incorporates an amount of sodium bicarbonate effective to provide a prescribed initial concentration of $HCO_3^-$ in the range of about 1 to 100 mm/L. The sodium bicarbonate is introduced into the solution from a syringe that is packaged within a gas-impermeable pouch.

The calibration solution disclosed in the Wong et al. patent works well for time periods of up to about 8 hours; however, over longer periods of time, e.g., 12 to 24 hours, the solution's pH value will rise excessively, and its corresponding pCO$_2$ will drop excessively. This is due primarily to the diffusion of $CO_2$ from the bag 17 that initially carries the solution and from the IV set 19 that carries the solution from the bag to the sensor assembly 21. Such diffusion necessarily occurs because the partial pressure of the $CO_2$ in the calibration solution is initially substantially higher than that of the $CO_2$ in the surrounding atmosphere. This variation in concentration has led to significant calibration errors.

A complicating factor in ascertaining the effect on calibration of this $CO_2$ diffusion is that the diffusion rate from the bag 17 is different from the diffusion rate from the IV set 19, which connects the bag with the sensor assembly 21. Generally, because of the substantially greater ratio of surface area to volume in the IV set, $CO_2$ diffuses substantially faster from the IV set than from the infusion fluid bag.

Figure 2:
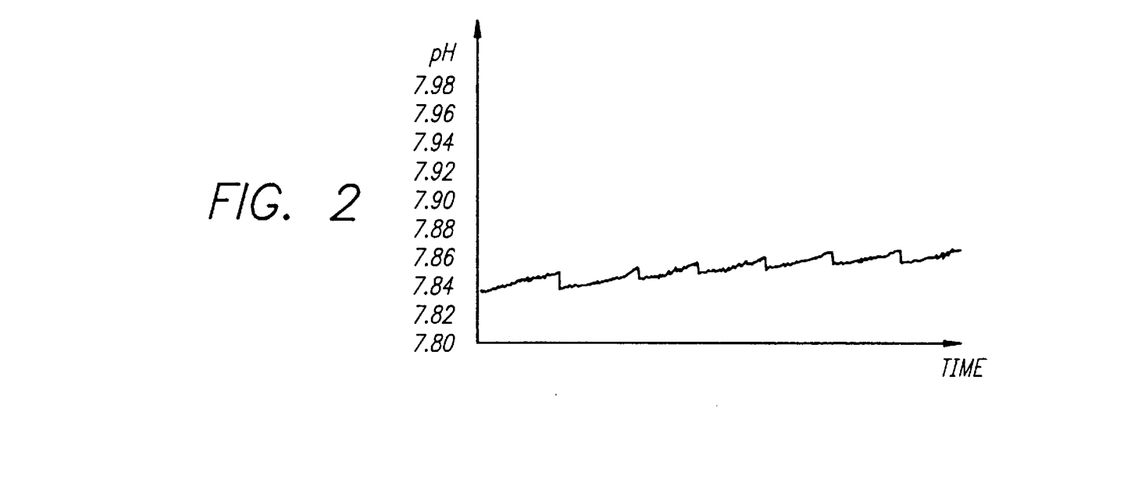
FIG. 2 is a graph depicting a typical increase over time in the pH of the infusion/calibration fluid adjacent to the $CO_2$ sensor of the sensor assembly of FIG. 1, due to the diffusion of carbon dioxide ($CO_2$) from the fluid bag and intravenous (IV) set.

FIG. 2 is a graph depicting the rise over time in pH of the calibrant located immediately adjacent to the $CO_2$ sensor of the sensor assembly 21, due to the diffusion of $CO_2$ from the calibrant within both the bag 17 and the IV set 19. It will be noted that the pH of the calibrant located adjacent to the $CO_2$ sensor normally rises at a slow, steady rate while the pump 13 pumps the fluid through the IV set and sensor assembly. During this time, the pH of the calibrant remaining within the bag likewise will rise, but at a significantly slower rate.

When the pump draws a blood sample from the patient 25 and then purges that sample back into the patient, a fresh supply of calibrant will be moved from the bag 17 into the position adjacent to the $CO_2$ sensor. The pH of that fresh supply of fluid will be lower than that of the calibrant that was injected into the patient by the purge; however, that lower pH will be slightly higher than the prior sample's initial pH, because of diffusion of $CO_2$ from the bag. This is depicted in FIG. 2.

The apparatus 11 of the invention overcomes the problem of $CO_2$ diffusion by incorporating such diffusion into a calculation of the expected $pCO_2$ of the calibrant that is at any time disposed adjacent to the $CO_2$ sensor of the sensor assembly 21. A theoretical, multi-compartment model is provided for the IV set 19, whereby the analyzer 27 maintains a running log of the status of each incremental amount of calibrant in the IV set. Conveniently, the calibrant in the IV set can be divided into incremental amounts, or slugs, of 1 ml each.

The calculation of $pCO_2$ for the slug of calibrant that finally reaches the $CO_2$ sensor of the sensor assembly 21 takes into account: 1) the diffusior coefficient for the calibrant bag 17, 2) the elapsed time in the bag, 3) the diffusioi coefficient for the IV set 19, and 4) the accumulated transit time in the IV set. The transit time in the IV set can vary widely depending on the duty cycle involved, ranging from as little as about 10 ml/hour during the normal slow pumping, to as much as 900 ml/hour during purge.

The calculation of $pCO_2$ for the slug of calibrant that finally reaches the $CO_2$ sensor also takes into account the temperature of the calibrant within the bag 17 and the temperature of the ambient atmosphere, which is assumed to be the same as that of the IV set 19. The ambient temperature generally is subject to greater variation than is the temperature of the bag. The signal produced by the $CO_2$ sensor generally varies directly with the temperature of the adjacent fluid. Signals indicative of bag temperature and ambient temperature are provided on lines 29 and 31 from temperature sensors 33 and 35, respectively. These temperature sensors conveniently can take the form of thermistors.

As will be appreciated by those of ordinary skill in the art, the diffusion coefficients for the calibrant bag 17 and for the IV set 19 can be determined either analytically or empirically. An analytical determination, of course, requires knowledge of the bag material (its surface area, thickness, porosity, etc.) and of the tubing that makes up the IV set (i.e., its length, thickness, diameter, porosity, etc.).

An empirical approach, on the other hand, requires the preliminary testing of the same or similar calibrant bag 17 and IV set 19. For example, a calibrant having a known initial $pCO_2$, as measured using a standard laboratory technique, can be placed in the bag or the IV set, and its $CO_2$ can be measured at periodic time intervals, again using a standard laboratory technique. This is for each of a plurality of fixed temperatures, e.g., 15, 20, 25 and 30° C. Thereby, a family of curves can be generated showing how $pCO_2$ of both the calibrant bag and the IV set will vary over time and temperature.

Each time the $CO_2$ sensor is to be calibrated, the $pCO_2$ of the particular incremental amount of calibrant then disposed adjacent to the $CO_2$ sensor of the sensor assembly 21 is calculated and correlated with the electrical signal then being produced by the sensor (e.g., using the family of empirically derived curves discussed above). This provides an indication of the $CO_2$ sensor's sensitivity and provides a calibration factor that can be used subsequently to adjust the signal produced when the patient's blood is withdrawn into the sensor assembly.

The pH sensor of the sensor assembly 21 is calibrated in an identical manner. The pH of the calibrant generally will vary in a predetermined, repeatable fashion with the calibrant's $pCO_2$. The relationship is given by the following formula:

(1) $\log(pCO_2) = -A(pH) + B$ where: $pCO_2$ is expressed in mmHg, and A and B are constants It has been determined that an IV set 19 newly put into use will absorb a substantial amount of $CO_2$ from the calibrant during the first one to two hours. To minimize the adverse effects of this absorption, it is desirable to pre-condition the IV set to the same $pCO_2$ and $pO_2$ atmosphere as that of the calibrant. Specifically, this can be achieved most conveniently by packaging the IV set in an atmosphere of about 0.5% -to- 1.0% $CO_2$, 21% $O_2$, and the balance $N_2$, sealed within a gas-impermeable pouch.

It also has been determined that the initial pH and $pCO_2$ of the calibrant are determined primarily by the pH and $pCO_2$ of the sodium bicarbonate syringe. It is desirable to control these levels so that the apparatus can initiate its operation each time at the same levels. To this end, it is considered desirable to store the syringe in an atmosphere having a predetermined $CO_2$ level, to stabilize the syringe's pH and $CO_2$ levels, and then to seal the syringe in a gas-impermneable pouch. The ideal gas atmosphere is considered to be 50%±20% $CO_2$, with the balance $N_2$.

Figure 3:
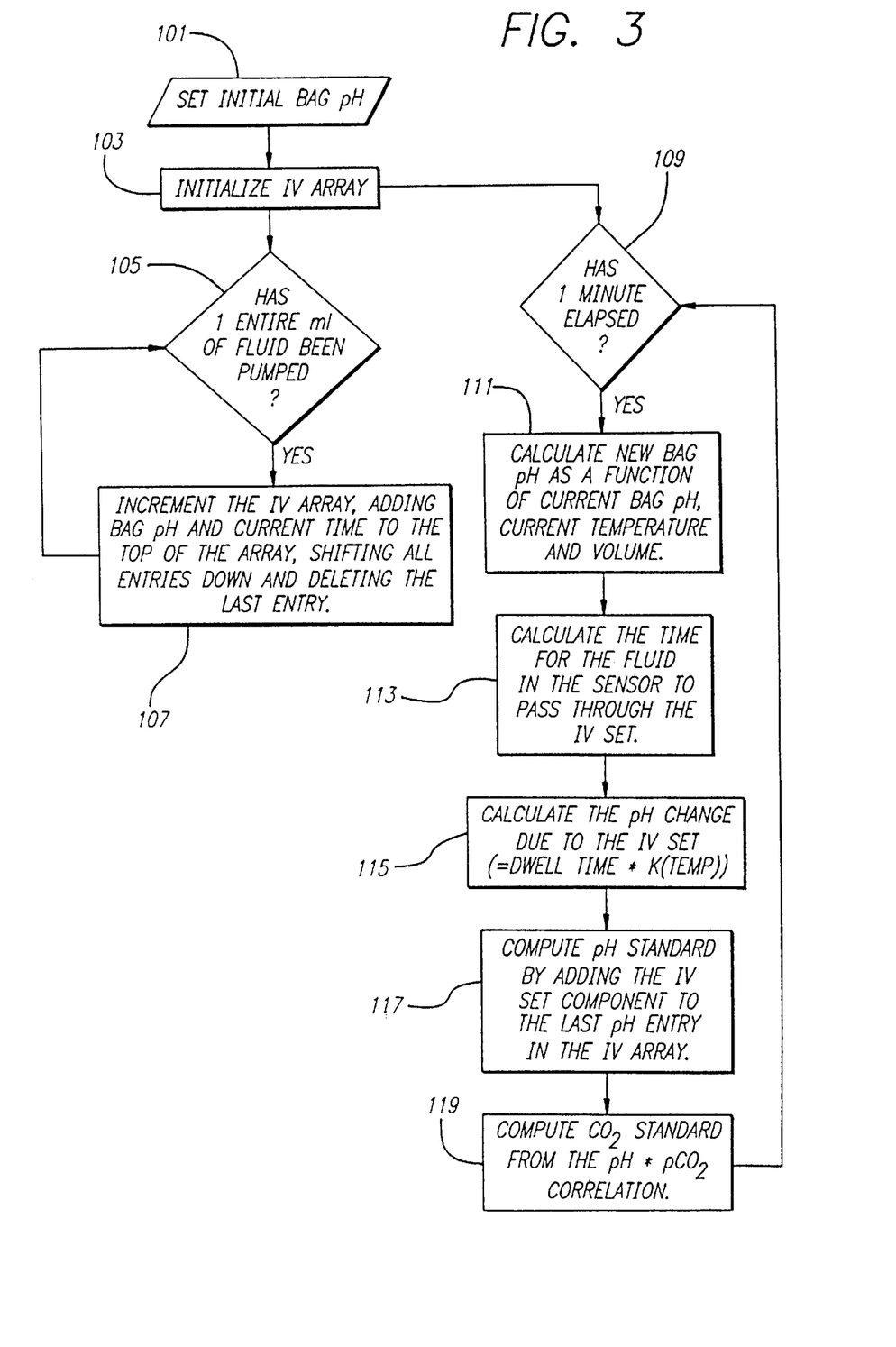
FIG. 3 is a simplified flowchart of the operational steps followed by the analyzer in calibrating the $CO_2$ sensor and the pH sensor of the sensor assembly of FIG. 1.

FIG. 3 is a simplified flowchart of the operational steps implemented by the analyzer 27 in calibrating the $CO_2$ sensor of the sensor assembly 21. In an initial step 101 of the calibration program, a value for the initial pH of the calibrant within the calibrant bag 17 is set. This value is determined based on the known amount of sodium bicarbonate injected into the bag from the syringe. Thereafter, in step 103, a pH table that carries data characterizing each incremental amount, or slug, of calibrant within the IV set 19 is initialized. Initially, the data for each slug should correspond to the pH of the calibrant then carried within the bag.

In a subsequent step 105, the analyzer 27 waits until the pump 13 has pumped a 1 ml slug of calibrant through the IV set 19. When that has occurred, the pH table is updated at step 107 by shifting all of its entries one step downward and by inserting the current time and the current pH of the fluid within the calibrant bag 17 to the pH table's top-most entry. The lower-most entry is deleted, and this process continues indefinitely. Thus, at any particular time, the lower-most entry in the pH table indicates the time at which the slug of calibrant then adjacent to the $CO_2$ sensor first entered the IV set, and it further indicates the pH of that slug and the ambient temperature at the time of that entry into the IV set.

While the analyzer 27 is implementing the procedures set forth in steps 105 and 107, as described above, it also determines, at step 109, on a time-interrupt basis, when one minute has elapsed. When it has, the program proceeds to step 111, where an updated pH is calculated for the calibrant still carried within the calibrant bag 17. This calculation takes into account the calculated pH from one minute earlier, the current temperature of the calibrant within the bag, as measured by the thermistor 33, and a calculation of the fluid volume remaining within the bag. The basis for this calculation is discussed above. It will be appreciated that the temperature of the calibrant within the bag affects the $CO_2$ diffusion rate and that the remaining calibrant volume affects the magnitude of the effect on pH of a given amount of $CO_2$ diffusion.

Thereafter, in step 113, the program calculates the amount of time the current slug of calibrant has been in transit within the IV set 19. Then, in step 115, the program calculates the actual change in pH caused by the calibrant's transit through the IV set. This change is affected, of course, by the dwell time within the IV set, as indicated by the data then carried in the lower-most entry in the IV set table. The change also is affected by the temperature of the calibrant within the IV set, which is assumed to be the arithmetic average of the current ambient temperature and the ambient temperature at the time the current slug of calibrant first entered the IV set. The basis for this calculation is discussed above.

Thereafter, in step 117, the program calculates the actual pH of the slug of calibrant then disposed adjacent to the $CO_2$ sensor, by combining the slug's calculated pH when it first entered the IV set 17 with the change in pH that was calculated to have occurred during its transit through the IV set. Finally, in step 119, the program calculates a $CO_2$ standard based on a correlation of pH with $pCO_2$. The relationship between the calibrant's $pCO_2$ and pH is given by the formula (1), set forth above.

As mentioned above, the $O_2$ sensor of the sensor assembly 21 also needs to be calibrated so that the signal it produces will have the requisite degree of accuracy. In this case, the amount of dissolved oxygen, i.e., $pO_2$, in the calibrant carried within the calibrant bag 17 ordinarily is close to that of the surrounding atmosphere. In addition, according to Henry's Law, dissolved oxygen varies inversely with the temperature at which the fluid is equilibrated.

If the calibrant bag 17 is stored at ambient temperature for a minimum period, say for 24 hours, it is reasonable to assume that the calibrant within the bag will have substantially the same ambient temperature. The parameter $pO_2$ then can be calculated accurately based on that temperature. This calculated value generally is fairly accurate, unless the calibrant undergoes a wide and sudden swing in ambient temperature, such as can occur for example when the bag is transported with the patient 25 from a relatively cold operating room (OR) to a relatively warm intensive care unit (ICU).

In that case, less oxygen can remain dissolved in the calibrant, so oxygen bubbles will form and attempt to diffuse outwardly through the calibrant bag 17 and the IV set 19. In some cases, however, an equilibrium at the higher temperature will not be reached before the calibrant reaches the sensor assembly 21, where further diffusion of oxygen is prevented because of the assembly's material. The calibrant within the assembly, therefore, will be supersaturated and will carry an excess $O_2$ partial pressure.

To overcome this problem, a special algorithm is used to account for the excess $pO_2$ during calibration of the $O_2$ sensor. This algorithm is depicted schematically in FIG. 4, which is a flowchart of the operational steps implemented by the analyzer 27 in determining the $pO_2$ of the calibrant located adjacent to the $O_2$ sensor of the sensor assembly 21.

Figure 4:
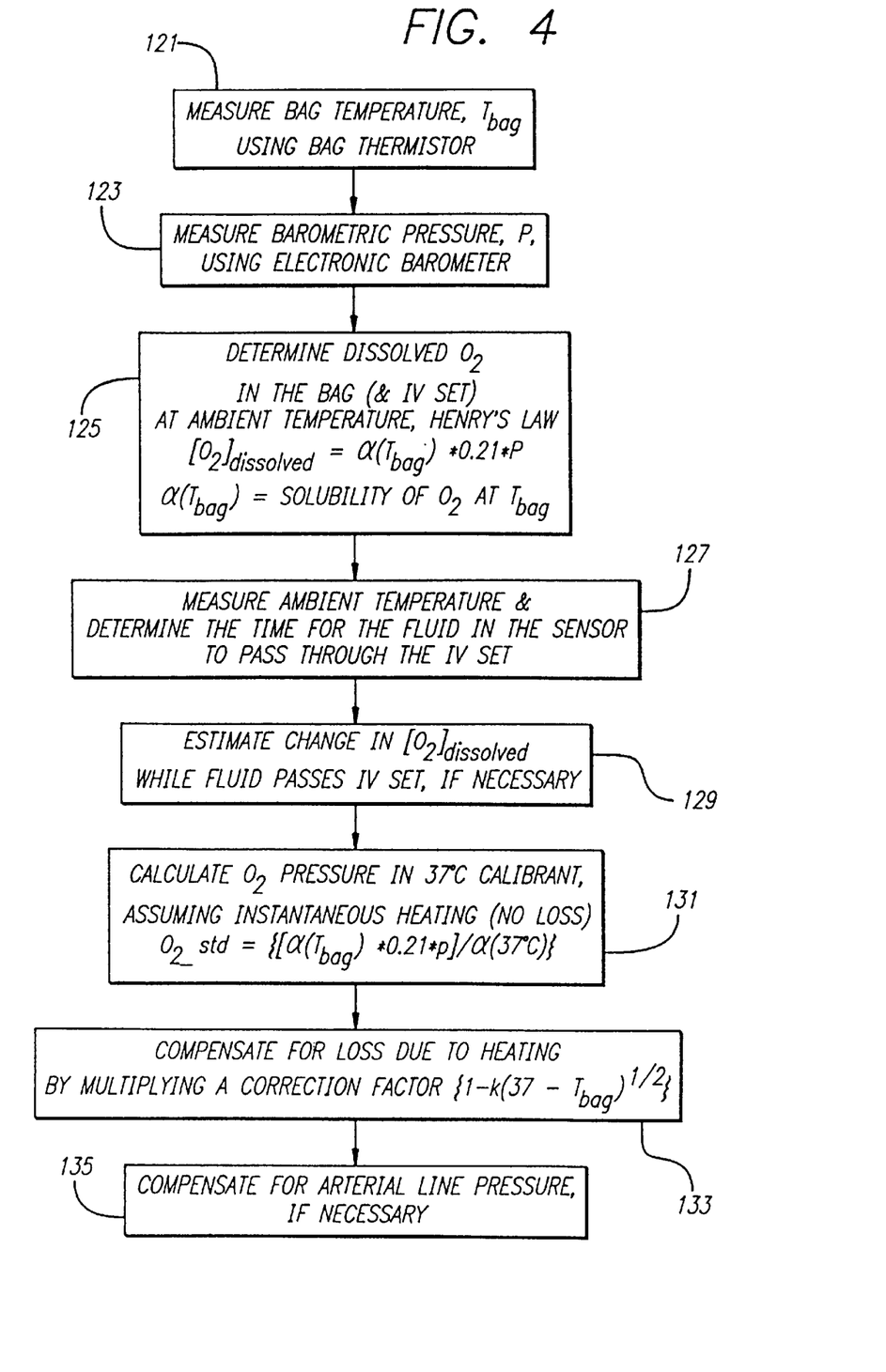
FIG. 4 is a simplified flowchart of the operational steps followed by the analyzer in calibrating the $O_2$ sensor of the sensor assembly of FIG. 1.

In carrying out the program, the analyzer 27 in step 121 measures the temperature $T_{bag}$, of the calibrant in the bag 17, using the thermistor 33 (FIG. 1), and in step 123 measures the barometric pressure P, using an electronic barometer (not shown in the drawings). Thereafter, in step 125, the analyzer determines the dissolved oxygen in the calibrant within the bag, using Henry's Law, as follows:

$$(2)\ pO_2 = \alpha(T_{bag})*0.21*P$$

where $\alpha(T_{bag})$=solubility of $O_2$ at $T_{bag}$

Thereafter, in step 127 of the program, the analyzer 27 measures the ambient temperature $T_{bag}$ and determines the accumulated transit time t, for the particular slug of calibrant that has just reached the $O_2$ sensor. Then, in step 129, the analyzer estimates the change in $pO_2$ that has occurred while that slug of calibrant has been disposed within the IV set 19. This change in $pO_2$ will result from any change in temperature from the temperature of the calibrant within the bag 17, and it is again determined using Henry's Law. This change in temperature is determined by monitoring the temperature of the IV set, which is assumed to correspond to the ambient temperature $T_{amb}$, as indicated by the signal from the thermistor 35 (FIG. 1).

When the calibrant finally enters the sensor assembly 21, its temperature is raised to about 37° C. by an electric heater (not shown) located within the assembly. This causes an immediate condition of $O_2$ supersaturation, because the excess $O_2$ cannot readily escape by diffusion. At step 131, the analyzer 27 calculates the resulting $pO_2$ using the following formula:

$$(3)\ O_{2std} = \{[\alpha(T_{bag})*0.21*P]\}/\alpha(37°\ C.)*F(T_{amb},t)$$

$F(T_{amb},t)$ represents change in $PO_2$ during transit through the IV set, and it is determined empirically based on the geometry of the sensor assembly and on the speed at which the calibrant's temperature is raised.

Thereafter, in step 133, the analyzer 27 compensates for any loss due to heating by multiplying this $pO_2$ value by the following correction factor:

$$(4)\ 1-[k*(37-T_{bag})^{1/2}]$$

Finally, in step 135 of the calibration program, the analyzer 27 compensates for the effects of any positive fluid pressure within the sensor assembly 21. Such a positive pressure might be required, for example, if the apparatus is being used to infuse the calibrant into an artery of the patient 25.

It should be appreciated from the foregoing description that the present invention provides an improved method for calibrating both a $CO_2$ sensor and an $O_2$ sensor that are part of an infusion fluid delivery and blood chemistry analysis apparatus. The method provides accurate calibration of these sensors by passing an infusible calibrant past them while correlating their resulting signals with calculated values of the calibrant's $pCO_2$ and $pO_2$. These calculations are specially made based on predetermined diffusion rates for the $CO_2$ and $)_2$ from an infusion bag and from an IV set that connects the bag with the sensors.

Although the invention has been described in detail with reference only to the presently preferred method, those skilled in the art will appreciate that various modifications can be made without departing from the invention. Accordingly, the invention is defined only by the following claims.

We claim:

1. A method for calibrating a sensor of a kind that measures a predetermined parameter of a test fluid, comprising:

placing a calibration solution in a container, wherein a predetermined parameter of the calibration solution has a predetermined value, and wherein the container is configured such that the value of the predetermined parameter can vary over time in a predetermined manner;

exposing the sensor to calibration solution supplied from the container, whereupon the sensor produces a calibration solution signal;

calculating the value of the predetermined parameter of the calibration solution supplied to the sensor based on its expected variation over time, and comparing the calculated value with the calibration solution signal actually produced by the sensor, to produce a calibration factor;

exposing the sensor to the test fluid, whereupon the sensor produces a test fluid signal; and adjusting the test fluid signal in accordance with the calibration factor, to produce a calibrated test fluid signal.

2. A method as defined in claim 1, wherein:

the predetermined parameter of the test fluid to be measured is $CO_2$ partial pressure;

the sensor is configured to measure $CO_2$ partial pressure;

the calibration solution has a predetermined initial concentration of $CO_2$;

the container has a porosity that allows $CO_2$ to escape from the calibration solution over time in a predetermined manner; and calculating includes calculating the concentration of $CO_2$ in the calibration solution supplied to the $CO_2$ sensor based on its expected escape from the container over time.

3. A method as defined in claim 2, wherein:

the container for the calibration solution includes a flexible bag and an intravenous line;

the flexible bag allows $CO_2$ to escape over time from the calibration solution it carries in a first predetermined manner, and the intravenous line allows $CO_2$ to escape over time from the calibration solution it carries in a second predetermined manner; and calculating includes calculating the concentration of $CO_2$ in the calibration solution supplied to the $CO_2$ sensor based on its expected escape over time from both the flexible bag and the intravenous line.

4. A method as defined in claim 3, wherein calculating includes determining the time durations the calibration solution supplied to the $CO_2$ sensor has dwelled in both the flexible bag and the intravenous line.

5. A method as defined in claim 2, wherein calculating includes measuring the temperature of the calibration solution in the container and determining the expected escape of $CO_2$ over time based on the measured temperature.

6. A method as defined in claim 2, and further including:

exposing a second, pH-responsive sensor to the calibration solution, whereupon the second, pH-responsive sensor produces a calibration solution pH signal;

calculating the pH of the calibration solution supplied to the second, pH-responsive sensor based on the expected escape of $CO_2$ from the container over time, and comparing the calculated pH with the calibration solution pH signal actually produced by the second, pH-responsive sensor, to produce a pH calibration factor;

exposing the second, pH-responsive sensor to the test fluid, hereupon the second, pH-responsive sensor produces a test fluid pH signal; and adjusting the test fluid pH signal in accordance with the pH calibration factor.

7. A method as defined in claim 1, wherein:

the calibration solution is infusible into a patient;

the test fluid is blood;

the method is implemented as part of an infusion fluid delivery apparatus that includes a sensor assembly that houses the $CO_2$ sensor;

exposing the sensor to calibration solution includes pumping the calibration solution through the sensor assembly and into the patient; and exposing the sensor to the test fluid includes drawing blood from the patient into the sensor assembly.

8. A method as defined in claim 1, wherein:

the sensor is configured to measure pH;

the calibration solution has a predetermined initial concentration of $CO_2$;

the container has a porosity that allows the $CO_2$ to escape from the calibration solution over time in a predetermined manner; and calculating includes calculating the concentration of $CO_2$ in the calibration solution supplied to the pH sensor based on its expected escape from the container over time, and calculating the pH of the calibration solution supplied to the pH sensor based on the calculated concentration of $CO_2$.

9. A method as defined in claim 8, wherein:

the container for the calibration solution includes a flexible bag and an intravenous line;

the flexible bag allows $CO_2$ to escape over time from the calibration solution it carries in a first predetermined manner, and the intravenous line allows $CO_2$ to escape over time from the calibration solution it carries in a second predetermined manner; and calculating includes calculating the pH of the calibration solution supplied to the pH sensor based on the expected escape of $CO_2$ over time from both the flexible bag and the intravenous line.

10. A method as defined in claim 9, wherein calculating includes determining the time durations the calibration solution supplied to the pH sensor has dwelled in both the flexible bag and the intravenous line.

11. A method as defined in claim 9, wherein calculating includes measuring the temperature of the calibration solution in the container and determining the expected escape of $CO_2$ over time based on the measured temperature.

12. A method as defined in claim 1, wherein:

the predetermined parameter of the test fluid to be measured is $O_2$ partial pressure;

the sensor is configured to measure $O_2$ partial pressure;

the calibration solution has a predetermined initial $O_2$ partial pressure;

the method further includes measuring the temperature of the calibration solution carried by the container;

the container has a porosity that allows the $O_2$ partial pressure of the calibration solution it carries to vary over time according to variations in the temperature of the calibration solution; and calculating includes calculating the $O_2$ partial pressure of the calibration solution supplied to the $O_2$ sensor based on the measured temperature of the calibration solution.

13. A method as defined in claim 12, wherein:

the container for the calibration solution includes a flexible bag and an intravenous line;

the flexible bag has a porosity that allows $O_2$ to pass through it over time in a first predetermined manner, and the intravenous line likewise has a porosity that allows $O_2$ to pass through it over time in a second predetermined manner; and calculating includes calculating the concentration of $O_2$ in the calibration solution supplied to the $O_2$ sensor based on its expected passage over time through both the flexible bag and the intravenous line.

14. A method as defined in claim 13, wherein calculating includes determining the time durations the calibration solution supplied to the $O_2$ sensor has dwelled in both the flexible bag and the intravenous line.

15. A method as defined in claim 12, wherein calculating includes measuring the temperature of the calibration solution in the container and determining the expected passage of $O_2$ over time through both the flexible bag and the intravenous line, based on the measured temperature.

16. A method as defined in claim 12, and further comprising:

measuring the pressure of the ambient environment; and adjusting the calculated value of $O_2$ partial pressure of the calibration solution based on the measured pressure of the ambient environment.

17. A method as defined in claim 1, wherein:

the predetermined parameter of the test fluid to be measured is the partial pressure of a predetermined gas;

the partial pressure of the predetermined gas in the calibration solution has a predetermined initial value;

the sensor is configured to measure the partial pressure of the predetermined gas;

the container has a porosity that allows the partial pressure of the calibration solution it carries to vary over time in a predetermined manner; and calculating includes calculating the partial pressure of the predetermined gas in the calibration solution supplied to the sensor based on its known variation over time.

18. A method for calibrating a sensor of a kind that measures a predetermined parameter of a patient's blood, comprising:

providing an infusion apparatus that includes an infusion fluid bag, an intravenous line, a sensor assembly that incorporates the sensor, and a pump;

placing a calibration solution in the infusion fluid bag, wherein a predetermined parameter of the calibration solution has a predetermined initial value, and wherein the value of the predetermined parameter of the calibration solution carried by the infusion fluid bag and the intravenous line can vary over time in a predetermined manner;

pumping the calibration solution from the infusion fluid bag through the intravenous line and the sensor assembly to the patient, whereupon the sensor produces a calibration solution signal;

calculating the value of the predetermined parameter of the calibration solution pumped through the sensor assembly based on its expected variation over time, and comparing the calculated concentration with the calibration solution signal actually produced by the sensor, to produce a calibration factor;

drawing blood from the patient into the sensor assembly, whereupon the sensor produces a blood signal; and adjusting the blood signal in accordance with the calibration factor.

19. A method as defined in claim 18, wherein:

the predetermined parameter of the blood to be measured is $CO_2$ partial pressure;

the sensor is configured to measure $CO_2$ partial pressure;

the calibration solution has a predetermined initial concentration of $CO_2$;

the infusion fluid bag has a porosity that allows $CO_2$ to escape from the calibration solution over time in a predetermined manner; and calculating includes calculating the concentration of $CO_2$ in the calibration solution supplied to the $CO_2$ sensor based on its expected escape from the infusion fluid bag over time.

20. A method as defined in claim 19, wherein:

the infusion fluid bag allows $CO_2$ to escape over time from the calibration solution it carries in a first predetermined manner, and the intravenous line allows $CO_2$ to escape over time from the calibration solution it carries in a second predetermined manner; and calculating includes calculating the concentration of $CO_2$ in the calibration solution supplied to the $CO_2$ sensor based on its expected escape over time from both the infusion fluid bag and the intravenous line.

21. A method as defined in claim 20, wherein calculating includes determining the time durations the calibration solution supplied to the $CO_2$ sensor has dwelled in both the flexible bag and the intravenous line.

22. A method as defined in claim 19, wherein calculating includes measuring the temperature of the calibration solution in the container and determining the expected escape of $CO_2$ over time based on the measured temperature.

23. A method as defined in claim 19, and further including:

exposing a second, pH-responsive sensor to the calibration solution, whereupon the second, pH-responsive sensor produces a calibration solution pH signal;

calculating the pH of the calibration solution supplied to the second pH-responsive sensor based on the expected escape of $CO_2$ from the infusion fluid bag over time, and comparing the calculated pH with the calibration solution pH signal actually produced by the second, ph-responsive sensor, to produce a pH calibration factor;

exposing the second, pH-responsive sensor to the blood, whereupon the sensor produces a blood pH signal; and adjusting the blood pH signal in accordance with the pH calibration factor.

24. A method as defined in claim 18, wherein:

the sensor is configured to measure pH;

the calibration solution has a predetermined initial concentration of $CO_2$;

the infusion fluid bag has a porosity that allows the $CO_2$ to escape from the calibration solution over time in a predetermined manner; and calculating includes calculating the concentration of $CO_2$ in the calibration solution supplied to the pH sensor based on its expected escape from the infusion fluid bag over time, and calculating the pH of the calibration solution supplied to the pH sensor based on the calculated concentration of $CO_2$.

25. A method as defined in claim 24, wherein:

the infusion fluid bag allows $CO_2$ to escape over time from the calibration solution it carries in a first predetermined manner, and the intravenous line allows $CO_2$ to escape over time from the calibration solution it carries in a second predetermined manner; and calculating includes calculating the pH of the calibration solution supplied to the pH sensor based on the expected escape of $CO_2$ over time from both the infusion fluid bag and the intravenous line.

26. A method as defined in claim 24, wherein calculating include determining the time durations the calibration solution supplied to the pH sensor has dwelled in both the infusion fluid bag and the intravenous line.

27. A method as defined in claim 24, wherein calculating includes measuring the temperature of the calibration solution in the infusion fluid bag and determining the expected escape of $CO_2$ over time based on the measured temperature.

28. A method as defined in claim 18, wherein:

the predetermined parameter of the blood to be measured is $O_2$ partial pressure;

the sensor is configured to measure $O_2$ partial pressure;

the calibration solution has a predetermined initial $O_2$ partial pressure;

the method further includes measuring the temperature of the calibration solution carried by the infusion fluid bag;

the infusion fluid bag has a porosity that allows the $O_2$ partial pressure of the calibration solution it carries to vary over time according to variations in the temperature of the calibration solution; and calculating includes calculating the $O_2$ partial pressure of the calibration solution supplied to the $O_2$ sensor based on the measured temperature of the calibration solution.

29. A method as defined in claim 28, wherein:

the infusion fluid bag has a porosity that allows $O_2$ to pass through it over time in a first predetermined manner, and the intravenous line likewise has a porosity that allows $O_2$ to pass through it over time in a second predetermined manner; and calculating includes calculating the concentration of $O_2$ in the calibration solution supplied to the $O_2$ sensor based on its expected passage over time through both the infusion fluid bag and the intravenous line.

30. A method as defined in claim 29, wherein calculating includes determining the time durations the calibration solution supplied to the $O_2$ sensor has dwelled in both the infusion fluid bag and the intravenous line.

31. A method as defined in claim 28, wherein calculating includes measuring the temperature of the calibration solution in the infusion fluid bag and determining the expected passage of $O_2$ over time through both the infusion fluid bag and the intravenous line, based on the measured temperature.

32. A method as defined in claim 28, and further comprising:

measuring the pressure of the ambient environment; and adjusting the calculated value of $O_2$ partial pressure of the calibration solution based on the measured pressure of the ambient environment.

33. A method as defined in claim 18, wherein:

the predetermined parameter of the blood to be measured is the partial pressure of a predetermined gas;

the partial pressure of the predetermined gas in the calibration solution has a predetermined initial value;

the sensor is configured to measure the partial pressure of the predetermined gas;

the infusion fluid bag has a porosity that allows the partial pressure of the calibration solution it carries to vary over time in a predetermined manner; and calculating includes calculating the partial pressure of the predetermined gas in the calibration solution supplied to the sensor based on its known variation over time.

* * * * *

UNITED STATES PATENT AND TRADEMARK OFFICE
CERTIFICATE OF CORRECTION

PATENT NO.    : 6,123,827

DATED         : September 26, 2000

INVENTOR(S)   : Wong et al.

It is certified that error appears in the above-identified patent and that said Letters Patent are hereby corrected as shown below:

At column 3, line 34, in part of the equation, the end bracket "]" should not be in superscript.
At column 4, line 60, "ay" should be "an".
At column 4, line 61, "puml" should be "pump".
At column 5, line 27, "measurec" should be "measured".
At column 7, line 28, "diffusior" should be "diffusion".
At column 7, line 29, "diffusioi" should be "diffusion".
At column 8, line 19, "determined" should be "determined."
At column 10, line 54, ")$_2$" should be "$O_2$".
Claim 6, line 66, "hereupon" should be "whereupon".
Claim 23, line 44, "ph-responsive" should be "pH-responsive".
Claim 26, line 8, "include" should be "includes".

Signed and Sealed this

Eighth Day of May, 2001

Attest:

NICHOLAS P. GODICI

Attesting Officer    Acting Director of the United States Patent and Trademark Office